United States Patent [19]

Deb

[11] Patent Number: 5,067,977

[45] Date of Patent: Nov. 26, 1991

[54] METHOD AND APPARATUS FOR MEASURING THE EFFICIENCY OF COOLING DEVICES

[75] Inventor: Sugato Deb, Perrysburg, Ohio

[73] Assignee: Libbey-Owens-Ford Co., Toledo, Ohio

[21] Appl. No.: 650,697

[22] Filed: Feb. 5, 1991

[51] Int. Cl.$^5$ ............................................. C03B 27/00
[52] U.S. Cl. ......................................... 65/29; 65/114; 65/158; 65/348; 374/126
[58] Field of Search ................... 65/158, 114, 349, 29, 65/350, 351; 374/124, 126; 250/341.1

[56] References Cited

U.S. PATENT DOCUMENTS

| | | | |
|---|---|---|---|
| 4,114,444 | 9/1978 | Schwenninger et al. | 65/158 X |
| 4,818,118 | 4/1989 | Bentel et al. | 250/341 X |
| 4,888,038 | 12/1989 | Herrington et al. | 65/349 |
| 4,974,182 | 11/1990 | Tank | 250/341 X |

*Primary Examiner*—Robert L. Lindsay
*Attorney, Agent, or Firm*—Marshall & Melhorn

[57] ABSTRACT

A method and apparatus for measuring the heat transfer in cooling devices. More particularly, the invention is concerned with the heat transfer pattern caused by blastheads used in the tempering of automotive glass. A thin foil sheet disposed in front of the blasthead is heated according to a predetermined pattern. One side of the foil sheet is then exposed to a cooling blast of air from the nozzles of the blasthead, while the temperature of the opposite side of the foil sheet is monitored using an infrared camera. Then, using information generated by the infrared camera, heat transfer information can be determined.

18 Claims, 1 Drawing Sheet

METHOD AND APPARATUS FOR MEASURING THE EFFICIENCY OF COOLING DEVICES

FIELD OF THE INVENTION

The present invention relates generally to a method and apparatus for determining the efficiency or effectiveness of cooling devices, and more particularly to a method and apparatus for determining the amount and distribution of cooling and the resulting heat transfer pattern created by the glass tempering blastheads in an adjacent sheet.

BACKGROUND OF THE INVENTION

Tempered glass is glass which results from the controlled cooling of glass to impart residual internal stresses wherein the surface areas are in compression and the internal areas are in tension. The compressive stresses near the surface of the glass serve to increase the strength of the glass sheet. When the glass breaks, the unbalanced stresses cause the glass sheet to break into small, relatively harmless fragments. Personal exposure to these small glass fragments is less likely to cause severe injury than exposure to the typically larger, more jagged fragments from an untempered glass sheet. For this reason, tempered glass is utilized in most automotive glass applications other than windshields.

In order to ensure adequate safety to the end user of automotive glass products, safety codes are becoming increasingly stringent in specifying the maximum size and configuration of fragments that are permissible upon the fracturing of tempered glass sheets. Whether a particular glass sheet can meet these standards is usually determined by the degree of temper in the glass.

In a typical tempering operation, the glass sheet is heated to a temperature above its strain point and near the glass softening temperature, and then rapidly chilled by simultaneously applying blasts of cold air against each of the opposing two surfaces of the sheet. Cooling the glass in this manner results in the outside surface of the glass being cooled below its strain point before the interior of the glass, consequently placing the surface areas of the glass in compression and the interior of the glass in tension.

There is in the automotive industry an ongoing desire to reduce the weight of components in the automobile which, in turn, has led to an increasing demand for thinner automotive glass. Unfortunately, thinner glass is more difficult to effectively temper, as the glass must be cooled more quickly to impart adequate stresses. There is, therefore, a need to develop more effective tempering techniques to provide glass components having the mechanical characteristics necessary to meet these requirements.

In glass tempering processes, the glass sheet may be positioned either vertically or horizontally. U.S. Pat. No. 4,888,038 discloses one such process, known as the horizontal press bending technique, wherein the glass is oriented horizontally and is tempered immediately after being press bent to utilize the residual heat in the sheet following bending. This technique generally includes first heating the pre-trimmed sheets of glass to their softening temperature by advancing them through a heating furnace. The heated glass sheets then travel to a bending area, where they are disposed between a pair of opposed complimentary mold members and pressed into parts with a desired shape and curvature. The shaped heated glass parts are then advanced from the bending area to the tempering area, where the glass is quickly chilled to below the annealing temperature of glass.

The tempering section typically includes two opposed blastheads disposed on opposite sides of the path of movement of the glass sheets. Each blasthead is provided with a plurality of tubes or nozzles operable to direct opposed streams of cooling fluid, such as air, toward and against the opposite surfaces of the glass sheet. Thus, for example, the horizontal press forming and tempering technique described above utilizes a pair of blastheads, one disposed above and one disposed below the path of the glass. The jets of air, when directed toward the two opposing surfaces of the glass sheet, quickly cool the glass, producing the desired temper. Each blasthead typically includes a source of air under pressure as well as a plurality of tubes positioned to direct streams of the pressurized air toward and against the surfaces of the glass sheets.

In designing blastheads for large scale production processes, various technical difficulties must be overcome. For example, it is well known that the density of air varies with altitude. A decrease in air density requires a corresponding increase in total air flow to achieve the proper amount of temper in the glass. Therefore, in designing the blastheads, attention must be directed to, among other things, the geographical location at which the tempering process is to be located, i.e., whether it will be, for example, at sea level or an altitude of five thousand feet.

In addition, because the tubes of the blastheads are oriented perpendicular to the surface of the glass, the impinging air is generally directed toward the glass at about a ninety degree angle. After contacting the glass surface the impinging air flows from the interior regions of the glass sheet towards the edges, creating an air flow transverse to the impinging jets, with linearly increasing velocity toward the edges of the sheet. As a result, the impinging air jets away from the central region of the glass are deflected toward the edges, causing a reduction in heat transfer near the edges. This change in heat transfer lessens the cooling effect in these areas, and consequently modifies the temper pattern. Thus, in conventional tempering operations utilizing blastheads, the temperature pattern across the glass is modified due to the effect of the escaping air. By altering the design of the blasthead and the positioning of the tubes, more or less cooling air can be applied to areas of the glass sheet that require greater or lesser tempering, respectively. In order to aid in the designing of more efficient blastheads, it would be advantageous to be able to analyze the heat transfer pattern created by a particular blasthead in an adjacent sheet.

Monitoring of glass temperatures could be accomplished by placing thermocouples at various locations on the surface of the glass sheet. However, attaching thermocouples in this way is a tedious, time consuming process, and information gathered by this technique is limited, since a thermocouple will only give a temperature for the point at which it contacts the glass. Therefore, to obtain a clear picture of temperatures over the entire glass surface, many thermocouples, spaced closely together, would have to be attached.

An alternative to using thermocouples for temperature measurement is the use of an infrared detection device, such as, for example, an infrared camera. The use of infrared cameras measuring radiant energy is generally well known as a method for determining temperatures. For example, U.S. Pat. No. 4,818,118 discloses use of a scanning infrared radiometer (also known as an IR camera) to measure the thickness of thermal barrier coatings. The thermal barrier coating is first heated by a laser source. Then, using an infrared camera, the radiant thermal energy of a region outside the laser strike region is measured at a predetermined time following termination of the heating pulse. The intensity of this measured radiant energy is compared with the radiant energy intensities which have been experimentally obtained from specimens of known thickness, and the thickness of the coating in question is inferred therefrom.

An infrared camera could similarly be used to obtain temperature information from a heated glass sheet. However, using an infrared camera to observe a sheet of hot glass in an actual production tempering process would be difficult if not impossible due to the hostile environment and the lack of space available for observation. It must be noted that the prior art referred to hereinabove has been collected and examined only in light of the present invention as a guide. It is not to be inferred that such diverse art would be assembled absent the motivation provided by the present invention.

SUMMARY OF THE INVENTION

The present invention relates to a method and apparatus for measuring heat transfer in cooling devices. More particularly, the invention is concerned with the heat transfer pattern caused by blastheads used in the tempering of automotive glass. A thin foil sheet-type heater disposed in front of the blasthead is heated according to a predetermined pattern. One side of the foil sheet is then exposed to a cooling blast of air from the nozzles of the blasthead, while the temperature of the opposite side of the foil sheet is monitored using an infrared camera. Then, using information generated by the infrared camera, heat transfer information can be determined.

BRIEF DESCRIPTION OF THE DRAWINGS

In the accompanying drawings, wherein like numerals are used to designate like parts throughout the same.

DESCRIPTION OF THE PREFERRED EMBODIMENT

Figure 1:
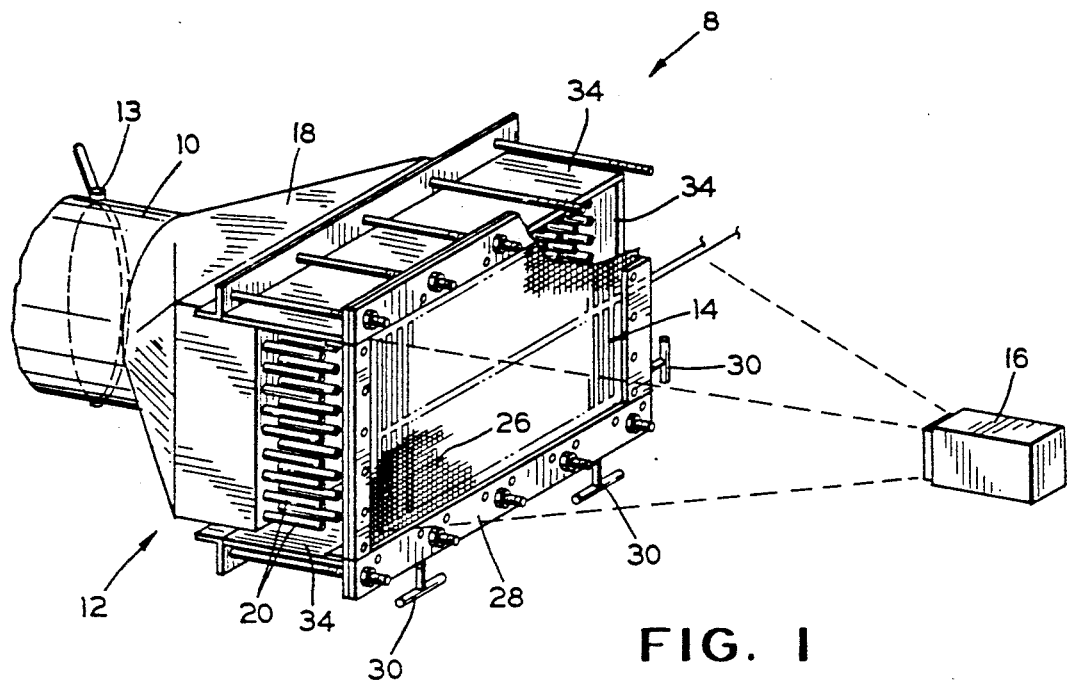
FIG. 1 is a perspective view of an apparatus for measuring heat transfer in accordance with the present invention.

Referring to FIG. 1, there is shown generally at 8 an apparatus in accordance with the invention comprising an air supply duct 10 for delivering pressurized air, from a fan or other pressurizing source (not shown), to a blasthead, identified generally at 12. The amount of air being delivered to the blasthead 12 is controlled at the fan or pressurizing source, by varying the amount of power supplied thereof. A butterfly valve 13, shown in phantom, is used to fine-tune the amount of air being delivered to the blasthead 12. A foil heater 14 is disposed adjacent the blasthead, and an infrared camera 16 is positioned to observe the surface of the foil heater opposite the blasthead. A typical blasthead 12 includes a metal hood or plenum 18 for receiving pressurized air from the duct 10, and a multiplicity of tubes 20 positioned to direct air generally normal to the surface of the foil heater 14. The tubes focus the quenching air into narrow streams and direct the streams toward the object to be cooled.

Figure 2:
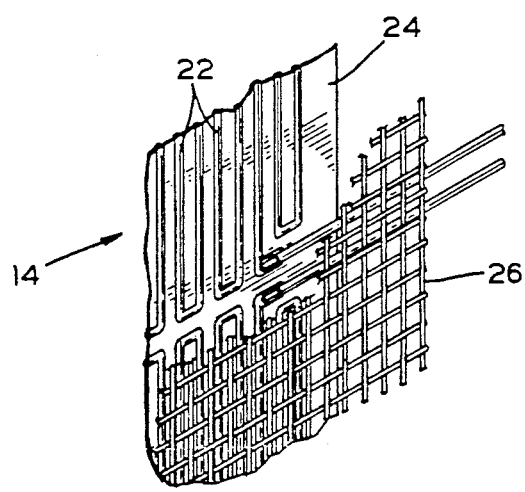
FIG. 2 is an enlarged fragmentary perspective view showing the foil heater and support grid of the invention.

In order to evaluate the cooling effect of a blasthead in accordance with the present invention, there is provided a substitute heated surface to simulate a hot glass sheet. For example, a foil heater 14 such as is commercially available from Minco Products, Inc, Minneapolis, Minn., having the product designation "Thermofoil Heater" (registered trademark), may suitably be employed. As illustrated in FIG. 2, the foil heater 14 consists of a serpentine pattern of thin, flexible etched-foil heating elements 22 laminated between insulating layers 24 such as Kapton or silicone rubber. The insulating layers 24 as illustrated are transparent, and therefore are not readily apparent in the drawings. The heating elements 22 are connected by leads to a suitable power source. When a sufficient amount of electric energy is applied to the foil heater 14, its temperature increases, due to resistance heating of the heating elements. While being exposed to the cooling air produced by the blasthead 12, the foil heater 14 will reach an equilibrium temperature of approximately 180° F. Ideally, the elements should be spaced closely together to provide for uniform heat transfer. Also, the insulation material should be kept relatively thin to minimize thermal gradients across the insulation material.

The temperature pattern of the surface of the foil heater opposite the blasthead will be representative of the surface of a glass sheet opposite a blasthead in a tempering operation in a steady state. In one type of tempering operation, the blastheads constantly emit an air blast while the glass sheet is moved between opposed blastheads, through the tempering station. In such a tempering operation, a preheated glass sheet enters the cooling or tempering zone of a glass forming operation, and moves between the blastheads while the air blast is constantly being applied. Consequently, the preheated glass sheet is cooled according to a particular pattern, that is, heat is removed over the entire sheet in accordance with a pattern which may not be uniform. The pattern of heat transfer by a particular blasthead from a stationary, uniformly heated object, as in accordance with the present invention, will correlate to the amount of heat transfer for the same blasthead during an actual glass tempering operation. Thus, the invention may be utilized to map or record, as by means of an infrared camera, the pattern of heat transfer which would occur in a glass sheet.

The foil heater 14 is supported in its proper position relative to the blasthead 12 by a support grid 26. The support grid 26 consists of a multiplicity of thin strands, preferably of plastic, interlaced with one another to form a tightly woven support structure. The foil heater 14 is attached to the support grid 26 using any of a variety of suitable fastening means such as, for example, stapling, stitching, or taping. In a preferred embodiment of the invention, the foil heater is glued to the support grid 26. The support grid 26 is, in turn, held in place by a support frame 28, which consists of four elongated, flat bars, preferably of a rigid material such as steel, which are rectangular in cross section and fastened together at each end to form a rectangular support structure around the periphery of the support grid 26. The support frame 28 is held in spaced relation in front of the tubes 20 by support rods 29 having threaded ends and extending from the plenum 18. The support frame 28 is secured in its desired location by tightening retaining nuts 30 on either side of the support frame 28. The support frame 28 typically is positioned so that the support grid 26, and thus the foil heater 14, are located equidistant from and adjacent to the openings of the tubes 20. In this position, the air streams emitted from the tubes 20 impinge upon the foil heater 14 substantially normal to the surface thereof, as they normally would upon a glass sheet during a typical glass tempering production operation. The distance from the tubes 20 to the support grid may readily be modified by loosening the retaining nuts 30 on the threaded rod, moving the frame 28 to the desired distance from the tubes, and retightening the nuts 30. By operating the invention at varying tube-to-glass distances, the optimum distance for a particular blasthead setup can be established. Threaded tensioners 31 are preferably located around the periphery of support grid 26, for fastening the peripheral edge of the support grid to the support frame 28. The threaded tensioners 31 are comprised of threaded rods which engage and extend through the support frame 26 such that the threaded rods are generally coplanar with the support grid 26. One end of the threaded rods is attached to the support grid 26, while the other end of the threaded rods attaches to the center of a bar, thereby forming a "T" shaped handle which may be used to turn the threaded tensioners 31. When the handle is properly turned, tension is supplied to the support grid 26 so that the foil heater 14 is kept taut and substantially flat.

The power input to the heating elements 22 is controlled so that the foil heater 14 generates a predetermined desired heat flux surface pattern. The impinging air streams affect the foil heater 14 in much the same manner as they would a glass sheet in a tempering process, generating a varying temperature profile across the surface. As one surface of the foil heater 14 is cooled by the blasts of air, the temperature of the opposite side is correspondingly modified. The temperature of this opposite surface is continuously monitored using a high resolution infrared camera 16 such as, for example, is available from Mikron Instrument Co., Inc., Wyckoff, N.J. The temperature information gathered by the infrared camera 16 is then stored in a computer. The temperature data may also be recorded in the form of a plat or map with differing temperatures represented by different colors for visual observation. The ability of the infrared camera to capture in high resolution and store the temperature data for the entire heating foil, and freeze it at any instant of time, is an advantageous feature for examining the heat transfer properties of an entire sheet of glass as well as localized points thereon.

The local heat transfer coefficient, h, for a localized area can be calculated using the formula:

$$h = q/\Delta T,$$

where
  q = input heat flux, and
  $\Delta T$ = temperature difference between the local foil surface temperature and the temperature of the impinging air.

The heat transfer information thus calculated for a particular blasthead, together with actual tempering performance of the particular blasthead on a production line, can be used to determine the manner in which different heat transfer profiles affect the temper pattern. For example, the amount of degradation in heat transfer for a particular blasthead, from the center area of the glass surface to the edges, can easily be determined. In addition, by running the test in an altitude chamber, conditions can be realistically simulated so that, before a facility is constructed in a high altitude area, a determination may be made as to whether effective tempering can be accomplished using a particular blasthead design. As further tests are run, it will become apparent which types of nozzle patterns, nozzle spacing, nozzle lengths, nozzle diameters, fluid pressure and velocity, temperatures, and humidities are the most effective, as well as how other tempering mediums, such as air mixed with fine water droplets, perform, how problems resulting from less effective tempering operations can be corrected, and so forth.

A particular advantage to using the present invention to determine heat transfer data is that, in order to evaluate a particular blasthead setup, only a small section or individual module of the actual blasthead setup needs to be built. This may typically be done by using an individual modular section of the actual blasthead, but enclosing a number of the sides from which air may escape, by air retaining walls 34. For example, if a blasthead is comprised of a number of modular sections any section along an outside edge, will be exposed to air streams from the neighboring sections. The effect of the air from these neighboring sections is to force air to escape away from the neighboring sections. This effect can be duplicated by employing a wall at any side where there would be a neighboring section, thus simulating the effect of the entire blasthead, while actually using only a small portion.

In accordance with the provisions of the patent statutes, the present invention has been described in what is considered to represent its preferred embodiment. However, it should be noted that the invention can be practiced otherwise than as specifically illustrated and described without departing from its spirit or scope. For example, other heating devices equivalent to the foil heater could be used, so long as they present a desired heating pattern and are easily positioned in front of the blasthead. Thus, a series of thin, closely spaced wires, or thin sheets of metal with attached busbars, capable of resistance heating when exposed to an electric current, could conceivably substitute for the foil heater. Similarly, infrared detection devices other than an infrared camera could be utilized.

In addition, the present invention could be used to evaluate the cooling effect of blastheads for bent or curved glass sheets. In such an application, the support grid could be shaped so that the foil heater would achieve the same shape as the glass surface it was meant to represent.

What is claimed is:

1. An apparatus for qualitatively and quantitatively defining the pattern of heat removal from a sheet-like member by an adjacent heat exchanger comprising:
  a sheet-like heating element adapted to represent said sheet-like member including means for heating the sheet-like element according to a predetermined pattern;
  a heat exchanger disposed opposite one of the major surfaces of said sheet-like element for causing heat to be removed from said sheet-like element over said one surface to thereby create a temperature pattern on said one surface, said removal of heat from said one surface creating a temperature pattern on the other major surface of said sheet-like element corresponding to the temperature pattern of said one surface; and a temperature sensing device for observing said other surface and indicating said temperature pattern on said other surface to thereby define said pattern of heat removal from said sheet-like element and thus said sheet-like member.

2. The apparatus according to claim 1, wherein said heat exchanger comprises an air cooling means.

3. The apparatus according to claim 2, wherein said air cooling means comprises a glass tempering blasthead.

4. The apparatus according to claim 1, wherein said sheet-like element comprises a foil heating device.

5. The apparatus according to claim 3, wherein said sheet-like element comprises a foil heating device.

6. The apparatus according to claim 4, wherein said foil heating device is comprised of thin, etched foil resistance heating elements laminated in an insulating material.

7. The apparatus according to claim 5, wherein said foil heating device is comprised of thin, etched foil resistance heating elements laminated in an insulating material.

8. The apparatus according to claim 6, wherein said temperature sensing device comprises an infrared camera.

9. The apparatus according to claim 7, wherein said temperature sensing device comprises an infrared camera.

10. An apparatus for defining the pattern of heat removal from a glass sheet by a glass tempering blasthead comprising:

a foil heating device composed of thin, etched foil resistance heating elements laminated in an insulating material;

a glass tempering blasthead disposed opposite one of the major surfaces of said foil heating device for causing heat to be removed from said foil heating device over said one surface, said removal of heat from said one surface creating a temperature pattern on the other major surface of said foil heating device corresponding to the temperature pattern of said one surface; and an infrared camera for observing said other surface and indicating said temperature pattern on said other surface to thereby define said pattern of heat removal from said foil heating device.

11. A method for defining the pattern of heat removal from a sheet-like member by an adjacent heat exchanger comprising the steps of:

heating a sheet-like element adapted to represent said sheet-like member according to a predetermined pattern;

directing cooling air against one of the major surfaces of said sheet-like element to remove heat from said one major surface;

simultaneously measuring the temperature over the other major surface of said sheet-like element; and determining the pattern of heat removal by the heat exchanger from the sheet-like element from the temperature of said other surface.

12. The method of claim 11, wherein the sheet-like element is heated by electrical energy.

13. The method of claim 11, wherein the cooling air is directed against said one major surface by a glass tempering blasthead.

14. A method for evaluating the efficiency of a glass tempering blasthead, comprising the steps of:

heating a thin-foil heating device according to a predetermined pattern;

removing heat from one of the major surfaces of said thin foil heating device by directing cooling air against said one major surface from a glass tempering blasthead; and simultaneously observing the other major surface of said sheet-like member with an infrared camera whereby the efficiency of the glass tempering blasthead can be calculated using the temperature information gathered by the infrared camera.

15. The apparatus according to claim 1, wherein said sheet-like member comprises a glass sheet.

16. The apparatus according to claim 15, wherein said sheet-like element comprises a foil heating device.

17. The apparatus according to claim 16, wherein said foil heating device is comprised of thin, etched foil resistance heating elements laminated in an insulating material.

18. The apparatus according to claim 17, wherein said temperature sensing device comprises an infrared camera.

* * * * *